(12) United States Patent
Mikulskis et al.

(10) Patent No.: US 7,906,630 B2
(45) Date of Patent: Mar. 15, 2011

(54) METHOD FOR IDENTIFYING PEPTIDES IN A BIOLOGICAL SAMPLE

(75) Inventors: Alvydas Mikulskis, West Roxbury, MA (US); Mary F. Lopez, Bedford, MA (US)

(73) Assignee: PerkinElmer Heath Sciences, Inc., Waltham, MA (US)

( * ) Notice: Subject to any disclaimer, the term of this patent is extended or adjusted under 35 U.S.C. 154(b) by 1237 days.

(21) Appl. No.: 11/114,629

(22) Filed: Apr. 26, 2005

(65) Prior Publication Data

US 2005/0282240 A1    Dec. 22, 2005

Related U.S. Application Data

(60) Provisional application No. 60/521,440, filed on Apr. 27, 2004.

(51) Int. Cl.
  *A23J 1/00*    (2006.01)
  *A61K 38/00*   (2006.01)
  *A61K 51/00*   (2006.01)
(52) U.S. Cl. .................. 530/416; 514/1.1; 424/1.69
(58) Field of Classification Search .............. 530/416
  See application file for complete search history.

(56) References Cited

U.S. PATENT DOCUMENTS

| | | | | |
|---|---|---|---|---|
| 3,419,471 A | * | 12/1968 | Matsuoka et al. | 435/206 |
| 3,515,643 A | * | 6/1970 | Ghielmetti et al. | 435/206 |
| 4,552,845 A | * | 11/1985 | Reid | 435/206 |
| 4,777,242 A | * | 10/1988 | Nelles | 530/351 |
| 6,913,890 B2 | * | 7/2005 | Hsieh | 435/6 |
| 6,995,018 B1 | * | 2/2006 | Fisher et al. | 435/7.1 |
| 2004/0009534 A1 | * | 1/2004 | Sato et al. | 435/7.1 |
| 2004/0069707 A1 | | 4/2004 | Naldrett | 210/638 |

OTHER PUBLICATIONS

Merchant M., and Weinberger S.R. ,"Recent advancements in surface-enhanced laser desorption/ionization-time of flight-mass spectrometry," Electrophoresis (2000), 21, 1164-1167.
Isaaq, H.J., Conrads, T.P. Prieto, D.A., Tirumalai, R., and Veenstra, T.D. "SELDI-TOF MS for Diagnostic Proteomics," Anal. Chem. 75: 149A-155A.
Liotta, L.A., Petricoin, E.F., Ardekani, A.M., Hitt, B.A., Levine, P.J., Fusaro, V.A., Steinberg, S.M., Mills, G.B., Simone, C., Fishman, D.A., Kohn, E.C. (2003), "General Keynote: Proteomic Patterns in Sera Serve as Biomarkers of Ovarian Cancer," Gynecologic Oncology (2003), 88: S25-S28.
Petricoin, E.F., Ardekani, A.M., Hitt, B.A., Levine, P.J., Fusaro, V.A., Steinberg, S.M., Mills, G.B., Simone, C., Fishman, D.A. Kohn, E.C., Liotta, L.A., "Use of proteomic patterns in serum to identify ovarian cancer," The Lancet (2002), 359:572-577.
Kozak, K.R., Amneus, M.W., Pusey, S.M., Su F., Luong, M.N., Luong, S.A., Reddy, S.T., Farias-Eisner, R., "Identification of biomarkers for ovarian cancer using strong anion-exchange ProteinChips: Potential use in diagnosis and prognosis," Proc. Natl. Acad. Sci. USA (2003), vol. 100, No. 21, 12343-12348.
Shiwa, M., Nishimura, Y., Wakatabe, R., Fukawa, A., Arikuni, H., Ota, H., Kato, Y., Yamori, T., "Rapid discovery and identification of a tissue-specific tumor biomarker from 39 human cancer cell lines using the SELDI ProteinChip platform," Biochem. Biophys. Res. Commun. 309 (2003) 18-25.
Diamandis, E.P., "Mass spectrometry as a diagnostic and a cancer biomarker discovery tool: Opportunities and potential limitations," Mol. Cell. Proteomics 3.4 (2004) 367-378.
Cottingham, K., "Clinical Proteomics: Are We There Yet?," Anal. Chem. 75 (2003) 472A-476A.
Pieper, R., Gatlin, C.L., McGrath, A.M., Makusky, A.J., Mondal, M., Seonarain, M., Field, E., Schatz, C.R., Estock, M.A., Ahmet, N., Anderson, N.G., Steiner, S., "Characterization of the human urinary proteome: A method for high-resolution display of urinary proteins on two-dimensional electrophoresis gels with a yields of nearly 1400 distinct protein spots," Proteomics (2004), 4, 1159-1174.
Herzog, A., Kuntz, S., Daniel, H., Wenzel, U., "Identification of biomarkers for the initiation of apoptosis in human preneoplastic colonocytes by proteome analysis," Int J Cancer (2004), 109:220-229.
Rui, Z., Jian-Guo, J., Yuan-Peng, T., Hai, P., Bing-Gen, R. "Use of serological proteomic methods to find biomarkers associated with breast cancer," Proteomics (2003), 3, 433-439.
Wu, P., Stenman, U.H., Pakkala, M., Narvanen, A., Leinonen, J. , "Separation of enzymatically active and inactive prostate-specific antigen (PSA) by peptide affinity chromatography," The Prostate (2004), 58, 345-353.
Labugger, R., Simpson, J.A., Quick, M., Brown, H.A., Collier, C.E., Neverova, i., Van Eyk, J.E. , "Strategy for analysis of cardiac troponins in biological samples with a combination of affinity chromatography and mass spectrometry," Clin. Chem. (2003), 49:873-879.
Adkins, J.N., Varnum, S.M., Auberry, K.J., Moore, R.J., Angell, N.H., Smith, R.D., Springer, D.L., Pounds J.G. , Toward a human blood serum proteome: Analysis by multidimensional separation coupled with mass spectrometry, Mol Cell Proteomics (2002), 1:947-955.
Peter, J., Unverzagt, C., Krogh, T.N., Vorm, O., Hoesel, W. , "Identification of precursor forms of free prostate-specific antigen in serum of prostate cancer patients by immunosorption and mass spectrometry," Cancer Res. (2001) 61:957-962.

(Continued)

*Primary Examiner* — Maury Audet
(74) *Attorney, Agent, or Firm* — Gifford, Krass, Sprinkle, Anderson & Citkowski, P.C.

(57) ABSTRACT

The invention provides a method for isolating a cargo peptide from a sample containing a cargo peptide-carrier protein complex. The method involves contacting a sample comprising a cargo peptide-carrier protein complex with a binding moiety selective for the carrier protein, under conditions wherein the carrier protein binds non-covalently to the binding moiety, and wherein the binding moiety is attached to a support, dissociating the cargo peptide from the cargo peptide-carrier protein complex, wherein the carrier protein remains bound to the binding moiety, and collecting the cargo peptide, whereby the cargo peptide is isolated from the sample.

23 Claims, 3 Drawing Sheets

OTHER PUBLICATIONS

Wang, M.Z., Howard, B., Campa, M.J., Patz, E.F. Jr., Fitzgerald, M.C., "Analysis of human serum proteins by liquid phase isoelectric focusing and matrix-assisted laser desorption/ionization-mass spectrometry," Proteomics (2003), 3:1661-1666.

Tirumalai, R.S., Chan, K.C., Prieto, D.A., Issaq, H.J., Conrads, T.P., Veenstra, T.D., "Characterization of the low molecular weight human serum proteome," Mol Cell Proteomics (2003), 2:1096-1103.

Kline, T.R., Pang, J., Hefta, S.A., Opiteck G.J., Kiefer, S.E., Schaller, J.E., "A high-yield method to extract peptides from rat brain tissue," Anal. Biochem. (2003), 315:183-188.

Anderson, N.L., Polanski, M., Pieper, R., Gatlin, T., Tirumalai, R.S., Conrads, T.P., Veenstra, T.D., Adkins, J.N., Pounds, J.G. Fagan, R., Lobley, A., "The Human Plasma Proteome: A Nonredundant List Developed by Combination of Four Separate Sources," Mol. Cell Proteomics (2004), 3:311-326.

Wang, Y.Y., Cheng, P., Chan, D.W., "A simple affinity spin tube filter method for removing high-abundant common proteins or enriching low-abundant for serum proteomic analysis," Proteomics (2003), 3, 243-248.

Sato, A.K., Sexton, D.J., Morganelli, L.A., Cohen, E.H., Wu, Q.L., Conley, G.P., Streltsova, Z, Lee, S.W., Devlin, M., DeOliveira, D.B., Enright, J., Kent, R.B., Wescott, C.R., Ransohoff, T.C., Ley, A.C., Ladner, R.C., "Development of mammalian serum albumin affinity purification media by peptide phage display," Biotechnol Prog. (2002), 18:182-192.

Nakamura, K., Suzuki, T., Kamichika, T., Hasegawa, M., Kato, Y., Sasaki, H., Inouye, K., "Evaluation and applications of a new dye affinity adsorbent," J. Chromatogr. A., (2002), 972:21-25.

Lollo, B.A., Harvey, S., Liao, J., Stevens, A.C., Wagenknecht, R., Sayen, R., Whaley, J., Sajjadi, F.G., "Improved two-dimensional gel electrophoresis representation of serum proteins by using ProtoClear," Electrophoresis (1999), 20:854-859.

Mehta, A.I., Ross, S., Lowenthal, M.S., Fusarao, V., Fishman, D.A., Petricoin, E.F. III, Liotta, L.A., "Biomarker amplification by serum carrier protein binding," Dis Markers (2002), 18:1-10.

Liotta, L.A., Ferrari, M., Petricoin, E., "Clinical Proteomics: Written in Blood," Nature (2003), 425:905.

Chertov O., Biragyn, A., Kwak, L.W., Simpson, J.T., Boronina, T., Hoang, V.M., Prieto, D.A., Conrads, T.P., Veenstra, T.D., Fisher, R.J. (2004), "Organic solvent extraction of proteins and peptides from serum as an effective sample preparation for detection and identification of biomarkers by mass spectrometry," Proteomics. (2004), 4, 1195-1203.

Burton, S.C. and Harding, D.R.K., "Hydrophobic charge induction chromatography: salt independent protein adsorption and facile elution with aqueous buffers," J. Chromatography A, vol. 814, Issues 1-2, Jul. 24, 1998, 71-81.

Tanaka, A.S., R. Andreotti, A. Gomes, R.J.S. Torquato, M.U. Sampaio, C.A.M. Sampaio. "A double headed serine proteinase inhibitor—human plasma kallikrein and elastase inhibitor—from *Boophilus microplus* larvae." Immunopharmacology 1999, vol. 45, pp. 171-177.

Gauthier, F. and K. Ohlsson. "Isolation and Some Properties of a New Enzyme-Binding Protein in Rat Plasma." Hoppe-Seyler's Zeitschrift Fuer Physiologische Chemie, Walter De Gruyter, Berlin, DE 1978, vol. 359, No. 8, pp. 987-992.

Bouhallab, S., G. Henry, E. Boschetti. "Separation of small cationic bioactive peptides by strong ion-exchange chromatography." Journal of Chromatography A 1996, vol. 724, pp. 137-145.

\* cited by examiner

METHOD FOR IDENTIFYING PEPTIDES IN A BIOLOGICAL SAMPLE

REFERENCE TO RELATED APPLICATION

This application claims priority to U.S. Provisional Patent Application Ser. No. 60/521,440, filed Apr. 27, 2004, which is incorporated herein by reference in its entirety.

BACKGROUND OF THE INVENTION

Early detection of disease is often an important factor in effective treatment. As such, screening for disease prior to the onset of outward symptoms has become routine practice for certain diseases, such as breast cancer and newborn metabolic disorders. Given that these and other screening practices have become successful, development of new and different types of screening tests applicable to varied types of disorders is ongoing in the medical research community. While most diagnostic and screening methods rely on detecting specific physiological or biochemical markers, recent research has shown the effectiveness of detecting disease by determining a profile of biochemical markers from a patient sample. This is possible because molecules contained in a patient sample can reflect a physiological state of the patient's body at the time of sample collection.

Peptide and protein biomarkers are emerging as indicators of the physiological state of biological systems, and therefore as diagnostic and prognostic markers. Recent developments in proteomics-based technologies have allowed analysis of complex protein samples and have thereby enabled biomarker profiling of tissues and biological fluids. An important aspect of biomarker profiling using these methods is sample preparation. How a specimen is prepared for analysis can determine the quality of a biomarker profile because these peptides are generally present in low concentrations relative to other proteins contained in biological specimens. Moreover, biological specimens generally contain certain proteins in high abundance, such as albumin in blood. It has been observed that high abundance proteins such as albumin often bind to peptides in the body, serving as carriers for these peptides. The particular peptides bound to high abundance proteins can be indicators of the physiological state of the patient, and therefore can serve as biomarkers. Thus, the ability to prepare samples containing peptides would facilitate discovery of biomarkers as well as development of clinical tests using biomarkers.

SUMMARY OF THE INVENTION

The present invention provides a method for isolating a cargo peptide from a sample containing a cargo peptide-carrier protein complex. The method involves contacting a sample comprising a cargo peptide-carrier protein complex with a binding moiety selective for the carrier protein, under conditions wherein the carrier protein binds non-covalently to the binding moiety, and wherein the binding moiety is attached to a support; dissociating the cargo peptide from the cargo peptide-carrier protein complex, wherein the carrier protein remains bound to the binding moiety; and collecting the cargo peptide from the support, whereby the cargo peptide is isolated from the sample.

The invention also provides a method for isolating a plurality of cargo peptides from a sample containing cargo peptide-carrier protein complexes. The method involves contacting a sample comprising cargo peptide-carrier protein complexes with a binding moiety selective for at least one carrier protein, under conditions wherein the at least one carrier protein binds non-covalently to the binding moiety, and wherein the binding moiety is attached to a support; dissociating the cargo peptides from the cargo peptide-carrier protein complexes, wherein the carrier proteins remain bound to the binding moiety; and collecting the cargo peptides from the support, whereby the cargo peptides are isolated from the sample.

The invention further provides a method for determining a biomarker profile. The method involves contacting a sample comprising cargo peptide-carrier protein complexes with a binding moiety selective for at least one carrier protein, under conditions wherein the at least one carrier protein binds non-covalently to the binding moiety, and wherein the binding moiety is attached to a support; dissociating the cargo peptides from the cargo peptide-carrier protein complexes, wherein the carrier proteins remain bound to the binding moiety; collecting the cargo peptides from the support, whereby the cargo peptides are isolated from the sample; and determining a mass spectrum of the isolated peptides, wherein peptides represented on the mass spectrum are identified as a biomarker profile. The method can further involve comparing the identified biomarker profile with a control biomarker profile.

The invention provides a method for isolating a plurality of cargo peptides from a serum sample. The method involves contacting a serum sample comprising cargo peptide-carrier protein complexes with an anion exchange moiety selective for at least one carrier protein, under conditions wherein the at least one carrier protein binds non-covalently to the anion exchange moiety, and wherein the anion exchange moiety is attached to a support; contacting the cargo peptide-carrier protein complexes with an elution solution having a pH greater than that of the sample, whereby the cargo peptides are dissociated from the cargo peptide-carrier protein complexes and the carrier proteins remain bound to the anion exchange moiety; and collecting the cargo peptides from the support, whereby the cargo peptides are isolated from the serum sample.

In an embodiment of a method of the invention, the binding moiety is an ion exchange moiety. The ion exchange moiety can be, for example, an anion exchange moiety or a cation exchange moiety. Exemplary anion exchange moieties useful in a method of the invention include diethylaminoethyl moiety, a diethylmethylaminoethyl moiety, a diethyl-[2-hydroxypropyl]aminoethyl moiety, an allylamine moiety and a quaternary ammonium moiety. In a particular embodiment, the anion exchange moiety includes a quaternary ammonium moiety. Exemplary cation exchange moieties useful in a method of the invention include a sulfonic acid moiety, a sulfopropyl moiety, a methyl sulfonate moiety, a carboxymethyl moiety and a phosphate moiety. A support useful in a method of the invention can be, for example, a membrane, gel, particle, surface or matrix.

In an embodiment of a method of the invention, dissociating can include contacting the cargo peptide-carrier protein complex with an elution solution.

In a specific embodiment in which an anion exchange moiety is used, the elution solution can have a pH greater than a pH of the sample. Such an elution solution can contain an alkaline species. In another specific embodiment in which a cation exchange moiety is used, the elution solution can have a pH lower than a pH of the sample. Such an elution solution can contain an acid species.

A method of the invention for isolating a cargo peptide can involve using a sample that contains a carrier protein that is a serum protein. Further examples of carrier proteins include a serum albumin, a fibronectin, a transferrin, an immunoglobulin, a Tamm-Horsfall glycoprotein, a fibrinogen, an alpha2-macroglobulin, a complement protein, a serpin, a haptoglobin, an alpha1-acid glycoprotein and a cerulopasmin.

A variety of samples can be used in a method of the invention. In one embodiment, the sample is obtained from a human individual. In other embodiments, the sample can include a bodily fluid, plasma or serum. A sample used in a method of the invention can include a sample loading solution, if desired.

The invention provides a commercial package useful for performing a method of the invention. In an embodiment, the commercial package includes an ion exchange support comprising a binding moiety selective for a carrier protein; and an elution solution adapted to dissociate a cargo peptide from a cargo peptide-carrier protein complex and to maintain association of the carrier protein with the binding moiety. The ion exchange support can be, for example, an anion exchange support, such as a quaternary ammonium moiety anion exchange support. In another embodiment, the ion exchange support is a cation exchange support.

A commercial package provided by the invention also can include an elution solution. In an embodiment in which an anion exchange material is provided, the elution solution contains an alkaline substance. In an embodiment, in which a cation exchange material is provided, the elution solution contains an acid substance.

A commercial package provided by the invention further can include a sample loading solution. In an embodiment, the elution solution has a pH higher than that of the sample loading solution and the package includes an anion exchange support. In another embodiment, the elution solution has a pH lower than that of the sample loading solution and the package includes a cation exchange support.

In an embodiment, the invention provides a commercial package that includes an anion exchange support; a sample loading solution; and an elution solution having a pH higher than that of the sample loading solution and capable of dissociating a peptide from a cargo peptide-carrier protein complex and of maintaining association of the carrier protein with the binding moiety.

In an embodiment, the invention provides a commercial package that includes a cation exchange support; a sample loading solution; and an elution solution having a pH lower than that of the sample loading solution and capable of dissociating a peptide from a cargo peptide-carrier protein complex and of maintaining association of the carrier protein with the binding moiety.

A commercial package of the invention can further include instructions for use.

In one embodiment, the invention provides a commercial package, including a quaternary ammonium anion exchange support and an elution solution having a pH of about 9-11, inclusive. In a particular embodiment, the elution solution has a pH of about 10.

DETAILED DESCRIPTION OF THE INVENTION

Figures 1A, 1B:
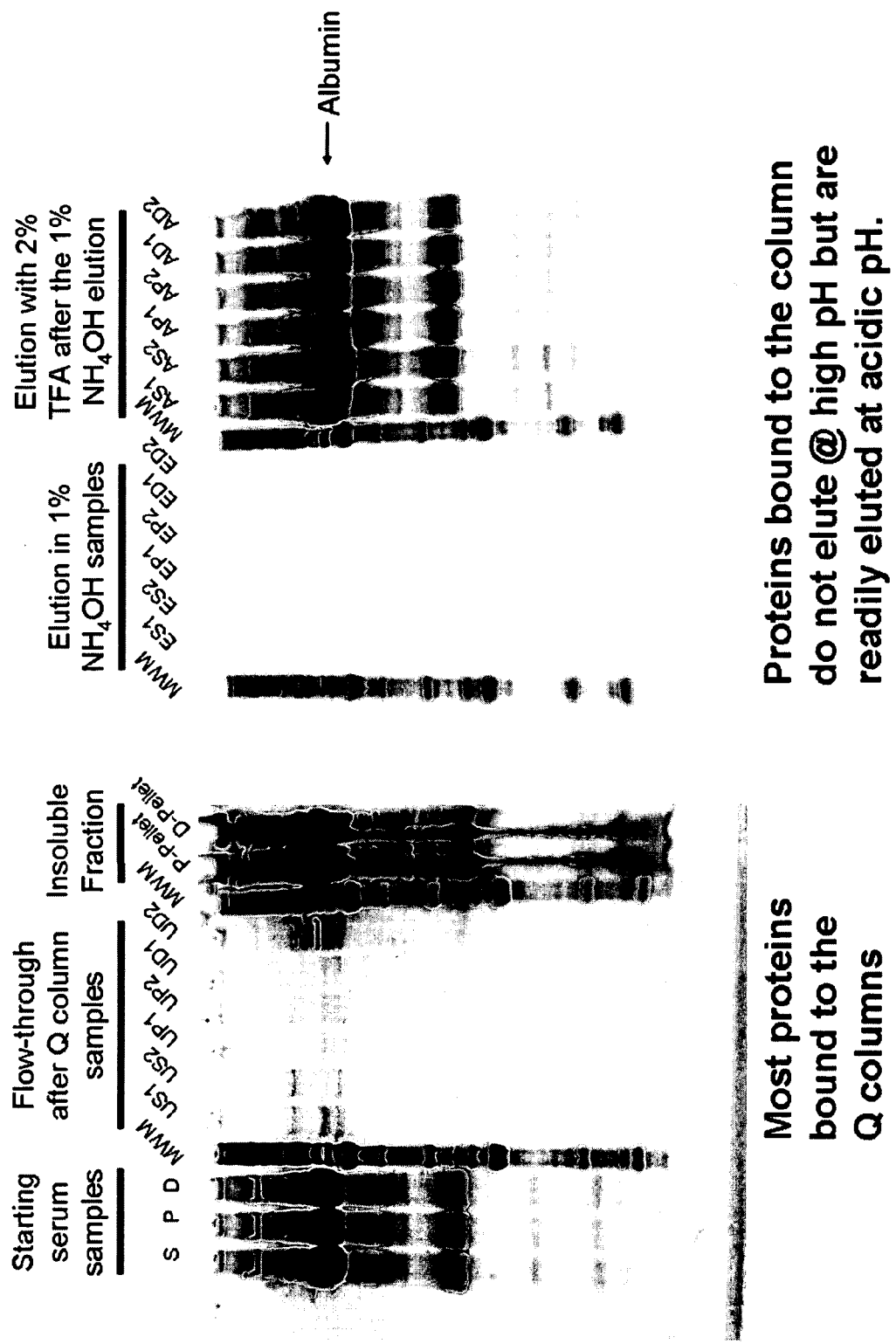
FIGS. 1A and B show stained SDS-PAGE gels representing proteins contained in serum samples prior to and throughout peptide isolation in accordance with an embodiment of the present invention.

The technology described herein relates to methods and commercial packages for isolating peptides from protein complexes in which the peptides exist as cargo associated with carrier proteins. Such complexes can be present, for example, in biological samples, such as body fluids and tissues of an individual. Separation of cargo peptides from such complexes can be useful for analyzing the biological samples. For example, it has been described previously that cargo peptides contained in cargo peptide-carrier protein complexes can serve as biomarkers indicative of a disease state (US 2004/0009534). Cargo peptides isolated according to methods described herein therefore can be used for a variety of purposes, including identification of new biomarkers and biomarker profiles applicable to development of forensic, diagnostic and prognostic biomarker assays.

As is described in the Example below, it has been found that cargo peptides can be isolated from cargo peptide-carrier protein complexes using an unexpected combination of anion exchange media with atypical elution solutions. More specifically, it has been found that cargo peptides can be isolated from serum by applying a serum sample to an anion exchange material at a pH of about 8, and eluting cargo peptides using a higher pH elution solution containing ammonium hydroxide. Generally described, cargo peptide-carrier protein complexes contained in the sample became bound to the anion exchange material via binding of the carrier proteins to the material. Other molecules in the serum sample were washed from the anion exchange material. Upon application of the higher pH elution solution, the cargo peptides were selectively eluted from the anion exchange material, leaving the carrier proteins bound to the material. The ability to specifically elute cargo peptides rather than cargo peptide-carrier protein complexes was unexpected because at high pH the protein binding capacity of an anion exchange material is low. The unexpected result that the proteins remained bound to the anion exchange material was confirmed when lower pH elution resulted in release of carrier proteins from the anion exchange material.

The methods described herein contrast with known procedures for preparing cargo peptides, in which a carrier protein (for example, albumin) is first dissociated from cargo protein by chemical dissociation, and then is separated from the cargo peptides by size fractionation chromatography (see, for example, Mehta et al. (2003-2004) *Dis Markers* 19:1-10; Liotta et al. (2003) *Nature* 425:905; and Chertov et al. (2004) *Proteomics* 4(4):1195-203.) Further, the procedure described herein contrasts with known methods in which serum albumin is covalently attached to an insoluble support prior to carrier protein elution (see, for example, US 2004/0009534).

In one embodiment, the invention provides a method for isolating cargo peptides from serum samples. The serum samples, which contain cargo peptides complexed with the high abundance carrier proteins such as albumin, are diluted and applied to a quaternary ammonium anion exchange material in a sample loading solution having about pH 7-8. The carrier proteins, in particular, albumin binds to the anion exchange material under these conditions. Thus the anion exchange material captures cargo peptide-carrier protein complexes as well as free carrier protein. The anion exchange material is washed with sample loading solution to remove unbound serum proteins and peptides. At this stage, cargo peptides are eluted from cargo peptide-carrier protein complexes by application of an elution solution containing 1% ammonium hydroxide. This treatment results in separation of cargo peptides from carrier proteins, and retention of carrier proteins on the anion exchange material. The resultant isolated peptides are then concentrated, if desired, and analyzed by mass spectrometry. Thus, this embodiment provides a method for isolating cargo peptides without any need for covalent linking of carrier protein to a support, nor any need for purifying cargo peptide from a sample containing dissociated cargo peptide-carrier protein complexes.

An embodiment of the invention provides a method for isolating a cargo peptide from a sample containing a cargo peptide-carrier protein complex. The method involves contacting a sample comprising a cargo peptide-carrier protein complex with a binding moiety selective for the carrier protein, under conditions wherein the carrier protein binds non-covalently to the binding moiety, and wherein the binding moiety is attached to a support, dissociating the cargo peptide from the cargo peptide-carrier protein complex, wherein the carrier protein remains bound to the binding moiety, and collecting the cargo peptide, whereby the cargo peptide is isolated from the sample.

Similarly, the invention provides a method for isolating a plurality of cargo peptides from a sample containing cargo peptide-carrier protein complexes. The method involves contacting a sample comprising cargo peptide-carrier protein complexes with a binding moiety selective for at least one carrier protein, under conditions wherein the at least one carrier protein binds non-covalently to the binding moiety, and wherein the binding moiety is attached to a support, dissociating the cargo peptides from the cargo peptide-carrier protein complexes, wherein the carrier proteins remain bound to the binding moiety, and collecting the cargo peptides, whereby the cargo peptides are isolated from the sample. The binding moiety can be selective for two or more carrier proteins, five or more carrier proteins, ten or more carrier proteins, or any number of carrier proteins as determined useful in a particular application of the method. For example, a binding moiety selective for one carrier protein can be used when obtaining a peptide sample for a relatively highly specific biomarker profile, such as an albumin biomarker profile. Alternatively, a binding moiety selective for multiple carrier proteins can be used when obtaining a peptide sample for a relatively broad biomarker profile, such as a whole serum biomarker profile.

A method of the invention can be used for isolating one or more species of cargo peptide. As used herein, the term "isolating" when used in reference to a cargo peptide means the act of separating the cargo peptide from other molecules, substances or materials in the sample to obtain the cargo peptide or cargo peptides in a purified form, such as a substantially pure form. The term purified does not require absolute purity, but rather is intended as a relative term. For example, the term purified can refer to a peptide sample having sufficient purity to produce peptide signals on a mass spectrometer. As used herein, the term "cargo peptide" means a peptide that is non-covalently bound to a carrier protein. The binding of a cargo peptide to a carrier protein generally occurs in the body fluid of an animal. Therefore, a cargo peptide is typically a naturally-occurring protein or portion thereof that binds to a carrier protein in a cell, fluid or tissue. However, a cargo peptide also can be an artificial protein or other macromolecule introduced into an individual, test organism, tissue or cell, for example as a drug, tracer, targeting molecule, diagnostic agent and the like.

The particular cargo peptide or peptides isolated using a method of the invention will depend on the type of sample used and goal of the study. The types and levels of cargo peptides present in a sample from an individual can be indicative of a particular health state, genetic disposition, or other physiological condition of the body. Therefore, determining the amount of a cargo peptide or profile of cargo peptides contained in a sample can be used to characterize a physiological condition of an individual. As such, a cargo peptide profile can serve as a characterization, forensic, diagnostic or prognostic tool. Accordingly, a cargo peptide prepared according to a method of the invention can be analyzed by any of various methods, including for example, and mass spectrometry, immunoanalysis, peptide sequencing, gel electrophoresis, chromatography and the like.

A variety of samples can be used when practicing a method of the invention. As used herein, the term "sample" means any biological fluid, cell, tissue, or fraction thereof, that includes one or more cargo peptide-carrier protein complexes. A sample can be, for example, a specimen obtained from an individual or can be derived from such a specimen. For example, a sample can be a bodily fluid, tissue section obtained by biopsy, or cells that are placed in or adapted to tissue culture. Such a sample can be a circulating fluid of the body which contains a cargo peptide-carrier protein complex, such as blood and lymph, as well as a fluid that remains associated with a tissue or organ, such as spinal fluid and breast fluid. Non-limited examples of samples include a sputum sample, a urine sample, a lymph sample, a cerebrospinal fluid sample, a milk sample, an ocular fluid sample, a semen sample, a vaginal secretion sample, an amniotic fluid sample, a synovial fluid sample, a nasal secretion sample, a bile sample, a tear sample, a nipple aspirate, an ascites fluid sample, a blood sample. In a specific embodiment, a sample used in a method of the invention is a bodily fluid.

A sample can be further fractionated, if desired, to a fraction containing particular cell types. For example, a blood sample can be fractionated into serum or into fractions containing particular types of blood cells such as white blood cells (leukocytes). If desired, a sample can be a combination of samples from an individual such as a combination of a tissue and fluid sample, and the like. In one embodiment, a sample used in a method of the invention is a serum sample. In another embodiment, a sample used in a method of the invention is a plasma sample.

For used in the methods of the invention, a sample can be processed to preserve or stabilize cargo peptide-carrier protein complexes. Methods for preserving the integrity of molecules in a sample are well known to those skilled in the art. Such methods include the use of appropriate buffers and/or inhibitors, including nuclease, protease and phosphatase inhibitors, that preserve or minimize changes in the molecules in the sample. Such inhibitors include, for example, chelators such as ethylenediamne tetraacetic acid (EDTA), ethylene glycol bis(P-aminoethyl ether)N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. A sample also can be processed to eliminate or minimize the presence of interfering substances.

Various methods for fractionating a fluid sample or cell extract are well known to those skilled in the art, including subcellular fractionation or chromatographic techniques such as ion exchange, hydrophobic and reverse phase, size exclusion, affinity, hydrophobic charge-induction chromatography, and the like (Scopes, Protein Purification: Principles and Practice, third edition, Springer-Verlag, New York (1993); Burton and Harding, J. Chromatoqr. A 814:71-81 (1998)). As an example, a serum sample from an individual can be fractionated to isolate leukocytes, if desired, or subfractionated, for example, into macrophages, T cells, B cells, eosinophils, and the like.

A sample can be obtained, for example, from a human; a veterinary animal, such as a dog, cat, horse, cow, pig, sheep, and goat; a research animal, such as a rat, mouse, guinea pig and rabbit; a plant, a fungus and a prokaryote. In one embodiment, a sample used in a method of the invention is obtained from a human individual.

A sample useful in a method of the invention can contain a cargo peptide-carrier protein complex in which binding between cargo peptide and carrier protein is direct or indirect. Binding between cargo peptide and carrier protein can be indirect, for example, when the cargo peptide is associated with a molecule(s) that binds to the carrier protein. In the case of indirect interaction, a molecule associated with a cargo peptide can be isolated with the cargo peptide or can remain bound to the carrier protein, depending on the conditions selected for dissociating the cargo peptide.

A sample used in a method of the invention contains at least one type of carrier protein. As used herein, the term "carrier protein" means a polypeptide that binds to a cargo peptide in a biological specimen. The particular carrier proteins present in a sample will depend on the origin of the sample because different biological fluids and tissues can contain different carrier proteins and different amounts of specific carrier proteins. Non-limiting examples of carrier proteins include serum proteins and urine proteins. Exemplary carrier proteins include an albumin, a fibronectin, a transferrin, an immunoglobulin, a Tamm-Horsfall glycoprotein, a fibrinogen, an alpha2-macroglobulin, a complement protein, a serpin, a haptoglobin, a hemopexin, an alpha1-acid glycoprotein, an alpha1-antitrypsin, alpha-fetoprotein, a cerulopasmin and the like. In one embodiment, a carrier protein is a serum protein.

The methods of the invention for isolating a cargo peptide involve non-covalently binding of the carrier protein portion of the cargo peptide-carrier protein complex to a binding moiety. As used herein, the term "binding moiety" when used in reference to a carrier protein means a molecular structure to which a carrier protein binds non-covalently and selectively. A binding moiety selective for the carrier protein can be, for example, a small molecule or portion thereof, or a macromolecule or portion thereof. Exemplary small molecules include dyes; drugs; ligands; and ion exchange moieties. As used herein, the term "ion exchange moiety" means a charged small molecule binding moiety selective for a carrier protein. Examples of ion exchange moieties, such as those present on ion exchange materials, are described herein below. Exemplary macromolecules include naturally-occurring and non-naturally occurring forms of nucleic acid, protein, carbohydrate; protein-nucleic acids and other artificial macromolecules.

A binding moiety selective for a carrier protein can be a generic or specific binding moiety. A generic binding moiety can bind selectively to one or more species of carrier protein contained in a sample. The term "selective binding" when used in reference to a generic binding moiety means that non-carrier proteins do not substantially bind to the binding moiety. As an example, a generic binding moiety can be adapted to bind any of various carrier proteins characterized by a particular physical property, such as the net charge of the carrier protein at a specified pH. Thus, in an embodiment, a binding moiety selective for a carrier protein can bind to more than one type of carrier protein. An exemplary generic binding moiety is an ion exchange moiety. In an embodiment, a method of the invention is performed using an ion exchange moiety. In a specific embodiment, the ion exchange moiety is an anion exchange moiety. Exemplary anion exchange moieties are described herein below.

A specific binding moiety can bind selectively to a particular carrier protein. The term "selective binding" when used in reference to a specific binding moiety means that proteins other than the defined protein do not substantially bind to the binding moiety. An exemplary specific binding moiety is an antibody directed to a particular carrier protein, such as an anti-albumin antibody directed to an albumin. A further exemplary specific binding moiety is protein A or protein G, each of which binds a particular species of immunoglobulin carrier protein. Such attachment is conveniently performed, for example, using any of various chemical crosslinking agents known in the art.

If desired, more than one binding moiety selective for a carrier protein can be used in a method of the invention. As examples, a plurality of antibodies directed to a plurality of species of carrier protein can be used, and a mixture of anion exchange moieties can be used.

A specific example of a binding moiety selective for a carrier protein is an ion exchange moiety. Anion exchange moieties are positively charged and are selective for negatively charged polypeptides. Cation exchange moieties are negatively charged and are selective for positively charged polypeptides. Depending on the charge characteristics of the carrier proteins contained in a sample, an appropriate ion exchange moiety can be selected by one skilled in the art. Non-limiting examples of anion exchange moieties include diethylaminoethyl moiety, a diethylmethylaminoethyl moiety, a diethyl-[2-hydroxypropyl]aminoethyl moiety, an allylamine moiety and a quaternary ammonium moiety. Non-limiting examples of cation exchange moieties include a sulfonic acid moiety, a sulfopropyl moiety, a methyl sulfonate moiety, a carboxymethyl moiety and a phosphate moiety.

An ion exchange moiety useful in a method of the invention can include a linker, such a polymer chain, if desired. Ion change moieties attached to polymer chains, which are in turn attached to a support, are known in the art and sometimes referred to as tentacle ion exchangers. In an embodiment, a method of the invention is performed using an anion exchange moiety listed above. In a specific embodiment, the anion exchange moiety is a quaternary ammonium moiety. In a further embodiment, a method of the invention is performed using a cation exchange moiety listed above.

A binding moiety used in a method of the invention generally is attached to a support. As used herein, the term "support" means a solid or semi-solid material to which a binding moiety selective for a carrier protein is attached, or which can be functionalized to include a binding moiety selective for a carrier protein. A support can be, for example, a natural or synthetic polymer, resin or silicate. Suitable supports are known in the art and illustratively include an agarose, such as is commercially available as Sepharose; a cellulose, illustratively including a carboxymethyl cellulose; a dextran, such as is commercially available as Sephadex; a polyacrylamide; a polystyrene; a polyethylene glycol; a resin; a silicate; divinylbenzene; methacrylate; polymethacrylate; glass; ceramics; paper; metals; metalloids; polyacryloylmorpholide; polyamide; poly(tetrafluoroethylene); polyethylene; polypropylene; poly(4-methylbutene); poly(ethylene terephthalate); rayon; nylon; poly(vinyl butyrate); polyvinylidene difluoride (PVDF); silicones; polyformaldehyde; cellulose acetate; nitrocellulose; and the like.

A "support" useful in a method of the invention can have a variety of physical formats, which can include for example, a membrane, a surface such as a tube, column or vessel, a hollow or solid bead, a fine particulate, a gel, a matrix. In an embodiment, a method of the invention is performed using a support that is a membrane. In another embodiment, a method of the invention is performed using a support that is a particle.

In one application of the methods of the invention, the binding moiety can be presented to the carrier protein whilst attached to the support. Alternatively, the support can be provided during or after the binding moiety is presented to the carrier protein, so long as the support is capable of selective attachment to the binding moiety. As an example, a binding moiety which is an antibody can be contacted with a carrier protein contained in a sample, and concurrently or subsequently can be associated with a selective support such as a bead conjugated to Protein A, G or a mixture thereof. Therefore, a support to which a binding moiety is attached can be provided at any convenient point while practicing a method of the invention.

A binding moiety can be attached to a support using a variety of well-known functional groups capable of interacting with a binding moiety to attach the binding moiety to the support, while leaving the binding moiety available to bind a carrier protein. Illustrative examples of functional groups include alkyl, Si—OH, carboxy, carbonyl, hydroxyl, amide, amine, amino, ether, ester, epoxides, cyanate, isocyanate, thiocyanate, sulfhydryl, disulfide, oxide, diazo, iodine, sulfonic or similar groups having chemical or potential chemical reactivity. Such functional groups can be reacted to attach a binding moiety to a support.

A binding moiety selective for a carrier protein generally will bind to the carrier protein under typical protein interaction assay conditions. Such conditions are well known to those skilled in the art and generally include roughly physiologically salt levels, a buffering agent, and a temperature in the range of 4 to 37° C. For a chosen binding moiety, a sample can be placed in or adjusted to produce a "sample loading solution" having a specified characteristic such as a specified pH or salt concentration. Therefore, in one embodiment, a method of the invention involves using a sample that includes a sample loading solution. Such a sample loading solution can include a buffer to adjust and/or maintain the sample at a specified pH. Non-limiting examples of buffers include ACES (N-(2-acetamido)-2-aminoethanesulfonic acid), ADA (N-(2-acetamido)iminodiacetic acid), BES (N,N-bis(2-hydroxyethyl)-2-aminoethanesulfonic acid), bicine (N,N-bis(2-hydroxyethyl)glycine), bis-tris, cacodylate, CAPS, CHES (2-(N-cyclohexylamino)ethane sulfonic acid), glycylglycine, glycinamide HCl, HEPES (4-(2-hydroxyethyl)piperazine-1-ethanesulfonic acid), HEPPS (N-(2-hydroxyethyl)piperazine-N'-(3-propanesulfonic acid), imidazole, MES (2-(N-morpholino)ethanesulfonic acid), MOPS (3-(N-morpholino) propanesulfonic acid), PIPES (piperazine-1,4-bis(2-ethanesulfonic Acid), POPSO (piperazine-N,N'-bis(2-hydroxypropanesulfonic acid), TAPSO (3-[N-Tris (hydroxymethyl)methylamino]-2-hydroxypropanesulfonic acid), TES (N-tris(hydroxymethyl)methyl-2-aminoethanesulfonic acid), tricine, tris, bicarbonate, phosphate and borate. A buffer generally is used in a concentration range of 1 to 500 millimolar depending on the desired conditions for binding of a carrier protein to its binding moiety. As is described below in relation to ion exchange media, it can be desired to use a buffer at low ionic strength, such as 5 mM and below, so long as the selected buffer maintains buffering capacity.

As is described in the Example below, an exemplary sample loading solution is a 20 mM sodium bicarbonate buffer, pH 8.3. Other exemplary sample loading solutions include 20 mM imidazole buffer, pH 7.2, and a 20 mM Tris; phosphate buffered saline, pH 7.2. For use with anion exchange materials, any buffer having a pH range of about 5 to 10 can be employed. For use with cation exchange materials, any buffer having a pH range of about 2 to 7 can be employed. In general, sample loading solution can be added in an amount of 0.01-1000 times the original volume of the sample, or in any other amount to achieve a sample of suitable characteristics for binding of the carrier protein to the binding moiety selective for the carrier protein.

In one embodiment, a sample containing a cargo peptide-carrier protein complex is contacted with an ion exchange binding moiety. For selecting conditions for ion exchange, those skilled in the art will understand that a suitable ion exchange moiety will generally have a charge opposite that of the carrier protein(s) of interest. For example, immunoglobulins, which generally have an overall positive charge, will bind well to cation exchangers, which contain negatively charged functional groups. In contrast, albumins, which generally have an overall negative charge, will bind well to anion exchangers. Because this interaction is ionic, binding takes place under low ionic conditions. Generally a sample containing a cargo peptide-carrier protein complex can be contacted with an anion exchange binding moiety at a pH between about 5 to 10. Alternatively, a sample containing a cargo peptide-carrier protein complex can be contacted with a cation exchange binding moiety at a pH between about 2 to 7. However, confirmation of an appropriate pH condition for a particular binding moiety can be performed empirically by those skilled in the art.

Any of the conventional buffers (typically concentration 0.5 mM up to 500 mM) can be used when using an ion exchange moiety. Positively charged buffering ions are generally used for anion exchanger moieties and negatively charged ones for cation exchange moieties. Phosphate buffers are generally used on both exchanger types. The highest salt concentration that permits binding of the protein of interest generally is used as the starting condition.

Contacting a carrier protein with a binding moiety selective for the carrier protein can be achieved by any of various conventional methods of bringing about contact between these components, such as pipetting the sample from a first container and depositing the sample in a second container, the second container having the support with one or more binding moieties Optionally, an equilibration solution can be used to obtain conditions suitable for allowing binding between a carrier protein and a binding moiety selective for the carrier protein. An equilibration solution can be used to wash a support and attached binding moiety in advance of carrier protein binding to the binding moiety, if desired. Further, an equilibration solution can be used to wash unbound material away from the support and bound carrier protein following binding of the carrier protein. An equilibration solution generally can have the same or similar pH as the sample as well as the same or similar salt concentration and buffer strength. Thus, for example, a sample loading solution including 200 mM sodium bicarbonate, pH 8.3 can be added to a sample to achieve a final concentration of the loading buffer in the sample of 20 mM sodium bicarbonate, and a corresponding equilibration solution can include 20 mM sodium bicarbonate, pH 8.3. Other combinations of sample loading and equilibration solutions will be recognized by one of skill in the art. In addition, more than one equilibration solution can be provided and used to wash a support with binding moiety. For example, a first equilibration solution having pH, salt and buffer concentrations which are the same or similar to the pH, salt and buffer concentrations in the sample is provided and used to wash a support and binding moiety and a second equilibration solution having pH, salt and buffer concentrations similar to an elution solution is provided and used to wash the support and binding moiety prior to binding of the carrier protein.

Allowing the carrier protein to bind to the binding moiety includes permitting the sample to remain in contact with the binding moiety for a sufficient period of time to achieve binding of the carrier protein to the binding moiety. As will be recognized by those of skill in the art, the period of time required for binding will depend on the conditions under which the binding reaction takes place, including such variables as temperature, salt concentration, and pH. Appropriate conditions and incubation time for binding can be determined using well known methods. Typically appropriate times are in the range of about 1 second to about 24 hours.

In general, reactions involving binding to a generic binding moiety, such as an ion exchange material are carried out under conditions determined by the identity of the material and the desired elution conditions. In particular, conditions will depend on the identity of the ion exchange material. In such an embodiment the pH of the sample can be adjusted by addition of a sample loading solution adapted to adjust the pH of the sample and maintain it at a desired pH while bringing the reactants into contact and allowing the carrier protein and carrier protein binding moiety to react.

The support with the binding moiety can be optionally equilibrated in a solution such as a buffer having the same or similar pH and salt concentrations as the sample so as to create the desired conditions for allowing a carrier protein to bind to a binding moiety selective for a carrier protein.

The methods of the invention involve dissociating a cargo peptide from a cargo peptide-carrier protein complex such that the carrier protein remains bound to the binding moiety. As used herein, the term "dissociating" when used in reference to a cargo peptide means disrupting the intermolecular bonds between the cargo peptide and a carrier protein. Such intermolecular bonds can be, for example, hydrogen bonds, dipole-dipole bonds, hydrophobic interactions and the like). Dissociating can be achieved by subjecting a cargo peptide-carrier protein complex to one or more physical or chemical conditions. Exemplary physical conditions for dissociating a cargo peptide include application of heat sufficient to break the association between the cargo peptide and carrier protein, for example, heat greater than 37° C., while maintaining the association of the carrier protein with its binding moiety, and application of electromagnetic energy, such as a laser pulse. Exemplary chemical conditions for dissociating a cargo peptide include application of a chemical denaturant sufficient to break the association between the cargo peptide and carrier protein, while maintaining the association of the carrier protein with its binding moiety. Non-limiting examples of chemical denaturants include a chaotropic agent, a high salt solution, a high pH solution (for example, pH>9), a low pH solution (for example, pH<5), and an organic solvent. In one embodiment in which an anion exchange moiety is employed, a high pH elution solution is used for dissociating a cargo peptide from a cargo peptide-carrier protein complex. The pH of the elution solution can be, for example, greater than about pH 9, about pH 9-14, about pH 10-14, about pH 11-14, about pH 12-14, about pH 13-14 and about pH 14. In another embodiment, in which a cation exchange moiety is employed, a low pH elution solution is used for dissociating a cargo peptide from a cargo peptide-carrier protein complex. The pH of the elution solution can be, for example, less than about pH 3, such as about pH 3-1, about pH 2, and about pH 1.

In one embodiment of a method of the invention for isolating a cargo peptide, dissociating is achieved by contacting the cargo peptide-carrier protein complex with an elution solution containing a chemical denaturant. The particular chemical denaturant contained in the elution solution will depend on the chemical characteristics of the binding moiety used. For example, if an anion exchange binding moiety is used, the elution solution has a high pH relative to pH used when contacting the sample with the binding moiety. Therefore, in an embodiment, a method of the invention is practiced using an elution solution having a pH greater than a pH of the sample.

An elution solution appropriate for use with an anion exchange material can contain, for example, an alkaline species such as ammonium hydroxide, sodium hydroxide, barium hydroxide, a triethylamonium salt, sodium carbonate, potassium carbonate or a combination thereof. A specific elution contains about 0.05-20% ammonium hydroxide. An elution solution described in the Example below contains about 1% ammonium hydroxide.

In an embodiment, a method of the invention is practiced using an elution solution that contains an alkaline species, such as a species selected from ammonium hydroxide, sodium hydroxide, barium hydroxide, a triethylammonium salt, sodium carbonate and potassium carbonate.

A support can provide a means for facile separation of isolated cargo peptide from carrier protein, and as is described above, can have a variety of physical formats, which can include for example, a membrane, a surface such as a tube, column or vessel, a hollow or solid bead, a fine particulate, a gel, a matrix. As such, a cargo peptide can be separated from a support using a variety of means, depending on the selected support. Typical procedures for collecting a cargo peptide include separating the cargo peptide from a reaction mixture containing a support. Such separating can involve removing a dissociated cargo peptide-containing liquid phase away from a solid or semi-solid support phase to which the carrier protein is bound. As an example, when a sample is contacted with a support that is a membrane, the sample can be applied to the membrane, and the dissociated cargo peptide separated from the membrane by centrifugal force, application of pressure, application of vacuum and the like.

As another example, when a sample is contacted with a support that is a particle or gel, the sample can be applied to the material in packed column format, and the dissociated cargo peptide separated from the column similarly by centrifugal force, application of pressure, application of vacuum and the like. As a further example, when a sample is contacted with a support that is a magnetic particle, the sample, can be applied to the material in solution, and the dissociated cargo peptide separated by magnetic removal of the material. Those skilled in the art will be able to adapt the methods described herein to a support of any kind using standard laboratory procedures.

A cargo peptide isolated as described herein can be useful for determining the number and/or amount of biomarkers present in a sample. Therefore, the invention provides a method for identifying a biomarker profile. The method involves contacting a sample comprising cargo peptide-carrier protein complexes with a binding moiety selective for at least one carrier protein, under conditions wherein the at least one carrier protein binds non-covalently to the binding moiety, and wherein the binding moiety is attached to a support, dissociating the cargo peptides from the cargo peptide-carrier protein complexes, wherein the carrier proteins remain bound to the binding moiety, collecting the cargo peptides, whereby the cargo peptides are isolated from the sample, and determining a mass spectrum of the isolated peptides represented on the mass spectrum are identified as a biomarker profile. The biomarker profile so identified can be compared with a control biomarker profile, such as a profile corresponding to a normal or disease health state. By such comparison, it can be possible to diagnose or predict the likelihood that an individual will be affected by a disease state, among other applications.

The invention provides a commercial package for isolating a cargo peptide. The package includes an ion exchange support comprising a binding moiety selective for a carrier protein; and an elution solution adapted to dissociate a cargo peptide from a cargo peptide-carrier protein complex and to maintain association of the carrier protein with the binding moiety.

The package can further include a sample loading solution adapted to allow binding of the carrier protein to the binding moiety selective for the carrier protein. If desired, the package can also include instructions for using the commercial package components for isolating a cargo peptide. Optionally included is an equilibration solution.

In one embodiment of a commercial package, an ion exchange support is provided. Typically, the ion exchange support is provided in a form illustratively including a membrane, a bead, a particulate solid, a gel, and a matrix. In one embodiment, the ion exchange support is an anion exchange support such as a material including an anion exchange moiety suitable for binding a carrier protein having an associated peptide. Exemplary ion exchange moieties include a diethylaminoethyl moiety, a diethylmethylaminoethyl moiety, a diethyl-[2-hydroxypropyl]aminoethyl moiety, an allylamine moiety and a quaternary ammonium moiety. In a specific embodiment, the commercial package includes an anion exchange support containing a quaternary ammonium moiety.

In a further embodiment, the supplied sample loading solution has a pH in the range of 5-11, inclusive and the supplied elution solution has a pH greater than that of the sample loading solution. In yet another embodiment, the supplied sample loading solution has a pH in the range of 2-7, inclusive and the supplied elution solution has a pH lower than that of the sample loading solution. Suitable sample loading solutions typically include a buffer such as ACES (N-(2-acetamido)-2-aminoethanesulfonic acid), ADA (N-(2-acetamido) iminodiacetic acid), BES (N,N-bis(2-hydroxyethyl)-2-aminoethanesulfonic acid), bicine (N,N-bis(2-hydroxyethyl) glycine), bis-tris, cacodylate, CAPS, CHES (2-(N-cyclohexylamino)ethane sulfonic acid), glycylglycine, glycinamide HCl, HEPES (4-(2-hydroxyethyl)piperazine-1-ethanesulfonic acid), HEPPS (N-(2-hydroxyethyl)piperazine-N'-(3-propanesulfonic acid), imidazole, MES (2-(N-morpholino)ethanesulfonic acid), MOPS (3-(N-morpholino) propanesulfonic acid), PIPES (piperazine-1,4-bis(2-ethanesulfonic Acid), POPSO (piperazine-N,N'-bis(2-hydroxypropanesulfonic acid), TAPSO (3-[N-Tris (hydroxymethyl)methylamino]-2-hydroxypropanesulfonic acid), TES (N-tris(hydroxymethyl)methyl-2-aminoethanesulfonic acid), tricine, tris, bicarbonate, phosphate and borate. A sample loading solution can be provided as a concentrated solution, if desired.

An elution solution is provided for eluting a cargo peptide from a cargo peptide-carrier protein complex, while maintaining binding of the carrier protein and binding moiety. The ingredients of an elution solution can vary depending on the ion exchange material provided. When an anion exchange support is provided, an elution solution generally contains an alkaline species such as ammonium hydroxide, sodium hydroxide, barium hydroxide, a triethylamonium salt, sodium carbonate, potassium carbonate, and the like or a combination thereof. When a cation exchange support is provided, an elution solution generally contains an acid species such as trifluoroacetic acid, trichloroacetic acid, acetic acid, hydrochloric acid and the like, or a combination thereof. As used herein the term "anion exchange support" means a support comprising a binding moiety selective for a carrier protein, which binding moiety is an anion exchange moiety. Exemplary anion exchange moieties are described herein above in relation to binding moieties selective for carrier proteins. As used herein the term "cation exchange support" means a support comprising a binding moiety selective for a carrier protein, which binding moiety is a cation exchange moiety. Exemplary cation exchange moieties are described herein above in relation to binding moieties selective for carrier proteins.

The methods described herein for isolating a cargo peptide can be performed using standard laboratory practices. Washing of columns, loading of samples, and elution of peptides can be carried out using centrifugal force, vacuum, pressure, or any other means causing the solutions to flow through the column, membrane or other support. Depending on the nature of the binding moiety, multiple washes with sufficient volumes of the sample loading solution or equilibration solution can be employed to remove loose polymeric substances in the material that can interfere with subsequent peptide analysis by mass spectrometry.

The methods described herein can be performed in any vessel suitable for containing the sample, support and solutions, and recovering the isolated peptide. A method of the invention can be performed in a single vessel or in multiple vessels. Exemplary commonly used vessels include a multi-well plate, tube, column, and capillary.

EXAMPLE

This example describes newly identified methods for isolating cargo peptides from cargo peptide-carrier protein complexes contained in biological samples.

To isolate cargo peptides from serum, samples prepared as described below were applied to a quaternary ammonium (Q) anion exchange material in Sample Loading Solution (pH 8); the anion exchange material was washed; and cargo peptides were eluted in Elution Solution having a high pH. Experiments were performed to confirm that the eluted peptides were indeed peptides formerly bound to carrier proteins and not free-floating serum-derived peptides. Three types of samples were used for these experiments—one was a serum sample and the other two were serum samples processed to remove low mass freely circulating peptides.

Serum samples were processed as follows to remove peptides having masses lower than 10K to 15K. Serum (500 microliters) was extensively dialyzed using 10K-cutoff SLIDE-A-LYZER Cassette (Pierce, Rockford, Ill.) or 15K-cutoff Spectra/Por dialysis bag. Five sequential 1-liter buffer changes were performed, with each dialysis step being at least 10 hours in duration. The first two dialyses were performed in phosphate buffer saline (PBS), the second two dialyses were performed in 20 mM Tris-HCl pH7.2 and the final dialysis was performed in 20 mM $NaHCO_3$ pH 8.3. The final volume of the recovered dialysate was about 680 microliters. The dialysate was clarified by centrifugation and the supernatant was used for further processing. The precipitated protein fraction was washed twice in 500 microliters of 20 mM NaHCO$_3$ pH 8.3 buffer and used for SDS-PAGE analysis.

The serum (S), 10 K dialysate (P) and 15 K dialysate (D) samples were then subjected to anion exchange conditions as follows. Six anion exchange Q-columns (Vivascience™, Carlsbad, Calif.) were pre-washed using two 500 microliter washes in 20 mM NaHCO$_3$ pH 8.3 buffer, one 500 microliter wash of 1% NH$_4$OH, followed by three 500 microliter washes in 20 mM NaHCO$_3$, pH 8.3 buffer. The P-, D-, and S-serum samples were diluted 1:10 in the 20 mM NaHCO$_3$, pH 8.3 buffer and loaded in duplicate on the pre-washed Q-columns using 700 microliters of the diluted dialyzed serum sample and 500 microliters of the diluted undialyzed serum sample per column. The 700 microliters vs. 500 microliters load volumes of dialyzed and undialyzed serum samples respectively were chosen to compensate for the dilution factor of the serum samples during the dialysis step. Binding of serum proteins to the Q-columns was performed by centrifugation at 2,000 RPM in a bench top centrifuge. The unbound material was collected as a flow-through fraction for the SDS-PAGE analysis. The Q-columns were then washed 6 times using 500 microliters of 20 mM NaHCO$_3$, pH 8.3 buffer. FIG. 1 panel A shows SDS PAGE analysis of starting serum samples (lanes S, P and Q), material that did not bind to the Q-columns ("Flow-through after Q column samples"), and the insoluble fraction of each sample. A comparison of lanes S, P and D shows that starting serum samples contained similar concentrations of protein. The minor amount of protein staining apparent in lanes US1-UD2 indicated and that most of the protein contained in each sample bound to the Q columns.

The cargo peptides were eluted from the Q columns as follows. After washing as described above, a 2-step elution was performed using 300 microliters of 1% NH$_4$OH solution per each elution step. The eluted fractions from both steps were combined for each sample and acidified by adding 25 microliters of 50% trifluoroacetic acid (TFA) per sample. About 20 microliters of each sample was saved for the SDS-PAGE analysis while the remainder of the sample was concentrated and desalted on a ZipPlate (Millipore, Bedford, Mass.) as recommended by the manufacturer. FIG. 1 panel B shows that little serum proteins were eluted in 1% NH$_4$OH solution. The eluted cargo peptides are not apparent on the SDS-PAGE gel because they would have electrophoresed out of the SDS-PAGE matrix due to their small molecular weights.

To confirm that carrier proteins remained bound to the Q column after elution with the 1% NH$_4$OH solution, the Q-columns were further eluted in a 2-step elution using 300 microliters of 2% TFA per each elution step. The eluted fractions were combined for each sample and 20 microliters of each sample was saved for the SDS-PAGE analysis while the remainder of the sample was concentrated and desalted on a ZipPlate as recommended by the manufacturer. FIG. 1 panel B shows that albumin and other proteins were eluted by the 2% TFA solution. This data confirms that albumin and other serum proteins remain bound to the Q column under conditions in which cargo peptides were eluted (1% NH$_4$OH).

Further detail on FIG. 1 follows: MWM=Benchmark Protein Ladder (Invitrogen Corporation, Carlsbad, Calif.); US1, US2, UP1, UP2, and UD1, UD2=Pairs of S-, P-, and D-serum proteins, respectively, not bound to the Q-columns; P-Pellet, D-Pellet=proteins precipitated during the dialysis of the P- and D-serum samples, respectively; ES1, ES2, EP1, EP2, and ED1, ED2=Replicate pairs of S-, P-, and D-serum proteins, respectively, eluted from the Q-columns using 1% ammonium hydroxide; AS1, AS2, AP1, AP2, and AD1, AD2=Replicate pairs of S-, P-, and D-serum proteins, respectively, eluted from the Q-columns in the second elution with 2% TFA after the 1% ammonium hydroxide elution: About 10 micrograms of S-, P-, and D-serum proteins before fractionation were loaded per lane. Equal volumes of unbound and fractionated proteins were loaded per each lane for convenient comparison of protein amounts in each sample. All samples were run on 4% to 12% gradient Bis-Tris gels (Invitrogen Corporation, Carlsbad, Calif.).

In summary, SDS-PAGE analysis results indicated that carrier proteins remained bound to the Q-columns during the 1% NH$_4$OH elution step but were eluted from the column using a 2% TFA solution.

Cargo peptides separated from carrier proteins by 1% NH$_4$OH elution as described above were analyzed by mass spectrometry using a prOTOF™ 2000 MALDI-TOF MS instrument. Samples were desalted and concentrated on a ZipPlate prior to analysis.

Figure 2A:
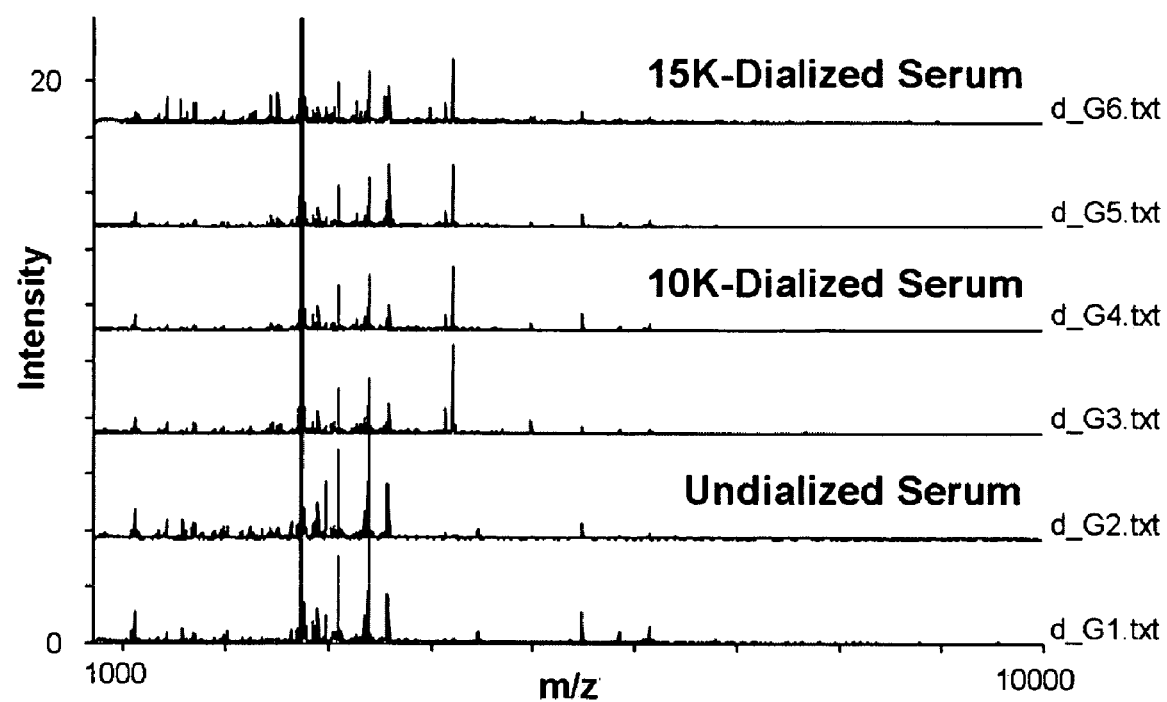
FIG. 2A shows mass spectra of dialyzed and undialyzed serum samples eluted from an anion exchange material using an elution solution having a pH greater than the pH of the sample loading solution.

FIG. 2 shows the resulting mass spectra. FIG. 2A shows samples of cargo peptides obtained from 15-K dialyzed serum, 10K-dialyzed serum and undialyzed serum analyzed in duplicate. Peptides in these samples appear as peaks in the range of 1000 to 5000 m/z. The significant overlap in the peptide peaks for dialyzed and undialyzed serum samples indicates that most of the peptides eluted with 1% NH$_4$OH were dissociated from cargo peptide-carrier protein complexes rather than from the freely-circulating peptides in the serum samples.

Figure 2B:
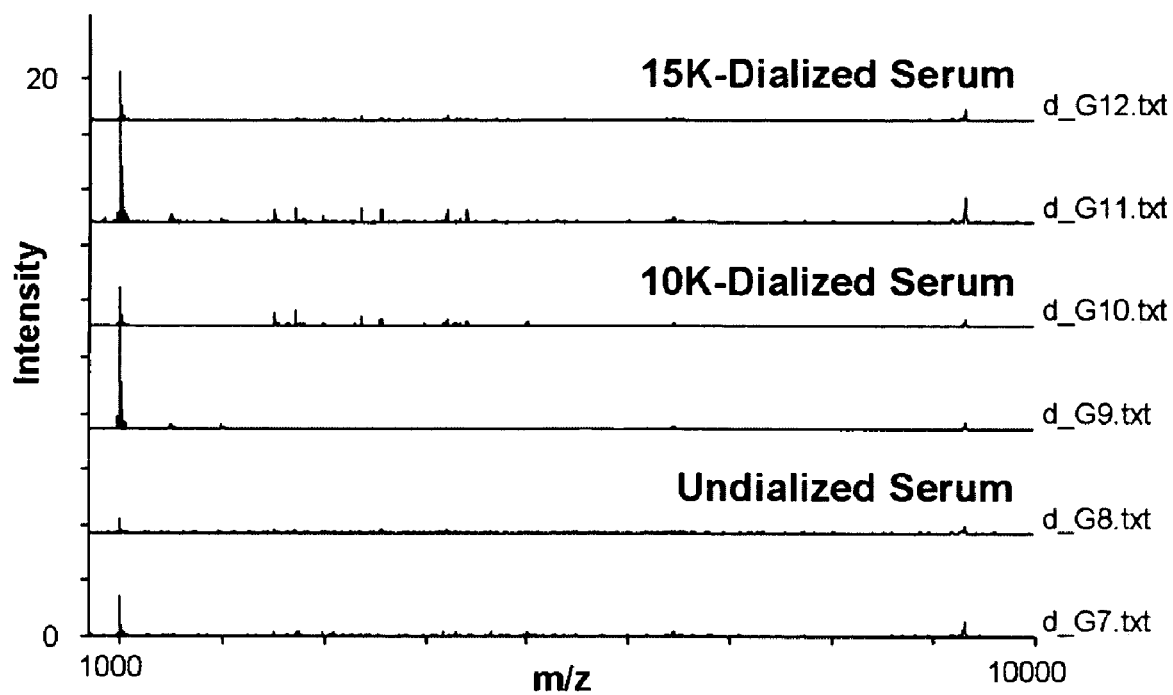
FIG. 2B shows mass spectra of samples obtained by further elution of protein samples from the anion exchange material using a low pH solution.

FIG. 2B shows mass spectra of samples eluted from the Q columns using 2% TFA, subsequent to 1% NH$_4$OH cargo peptide elution. Samples represented in this analysis include duplicates 15-K dialyzed serum, 10K-dialyzed serum and undialyzed serum. The spectra show trace levels of peptides recovered in the protein-rich acidic elution using the 2% TFA.

In summary, mass spectrometry analysis confirmed that cargo peptides were isolated from their cargo peptide-carrier protein complexes by high pH elution from an anion exchange material, while carrier protein remained associated with the anion exchange material.

Any patents or publications mentioned herein are incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The methods and commercial packages described herein are representative, and are not intended as limitations on the scope of the invention. Changes therein and other uses will occur to those skilled in the art. Such changes and other uses can be made without departing from the scope of the invention as set forth in the claims.

What is claimed is:

1. A method for isolating a cargo peptide from a sample containing a cargo peptide-carrier protein complex, comprising:
   contacting a sample comprising a cargo peptide-carrier protein complex with a binding moiety selective for the carrier protein, under conditions wherein the carrier protein binds non-covalently to the binding moiety, and wherein the binding moiety is attached to a support,
   dissociating the cargo peptide from the cargo peptide-carrier protein complex, wherein the carrier protein remains bound to the binding moiety, and
   collecting the cargo peptide, whereby the cargo peptide is isolated from the sample.

2. The method of claim 1, wherein the binding moiety is an ion exchange moiety.

3. The method of claim 2, wherein the ion exchange moiety is an anion exchange moiety.

4. The method of claim 3, wherein the anion exchange moiety comprises a moiety selected from a diethylaminoethyl moiety, a diethylmethylaminoethyl moiety, a diethyl-[2-hydroxypropyl]aminoethyl moiety, an allylamine moiety and a quaternary ammonium moiety.

5. The method of claim 4, wherein the anion exchange moiety comprises a quaternary ammonium moiety.

6. The method of claim 2, wherein the ion exchange moiety is a cation exchange moiety.

7. The method of claim 6, wherein the cation exchange moiety is selected from the group of a sulfonic acid moiety, a sulfopropyl moiety, a methyl sulfonate moiety, a carboxymethyl moiety and a phosphate moiety.

8. The method of claim 1, wherein the support is selected from a membrane, gel, particle, surface and matrix.

9. The method of claim 1, wherein the sample further comprises a sample loading solution.

10. The method of claim 1, wherein the dissociating comprises contacting the cargo peptide-carrier protein complex with an elution solution.

11. The method of claim 10, wherein the elution solution has a pH greater than a pH of the sample.

12. The method of claim 11, wherein the elution solution comprises an alkaline species.

13. The method of claim 12, wherein the alkaline species is selected from the group of ammonium hydroxide, sodium hydroxide, barium hydroxide, a triethylammonium salt, sodium carbonate and potassium carbonate.

14. The method of claim 10, wherein the elution solution has a pH lower than a pH of the sample.

15. The method of claim 14, wherein the elution solution comprises an acid species.

16. The method of claim 15, wherein the acid species is selected from the group of trifluoroacetic acid, trichloroacetic acid, acetic acid and hydrochloric acid.

17. The method of claim 1, wherein the carrier protein is a serum protein.

18. The method of claim 1, wherein the carrier protein is selected from a serum albumin, a fibronectin, a transferrin, an immunoglobulin, a Tamm-Horsfall glycoprotein, a fibrinogen, an alpha2-macroglobulin, a complement protein, a serpin, a haptoglobin, an alpha1-acid glycoprotein and a ceru-lopasmin.

19. The method of claim 1, wherein the sample is obtained from a human individual.

20. The method of claim 1, wherein the sample comprises a bodily fluid.

21. The method of claim 20, wherein the sample comprises plasma or serum.

22. A method for isolating a plurality of cargo peptides from a sample containing cargo peptide-carrier protein complexes, comprising:
   contacting a sample comprising cargo peptide-carrier protein complexes with a binding moiety selective for at least one carrier protein, under conditions wherein the at least one carrier protein binds non-covalently to the binding moiety, and wherein the binding moiety is attached to a support;
   dissociating the cargo peptides from the cargo peptide-carrier protein complexes, wherein the carrier proteins remain bound to the binding moiety; and
   collecting the cargo peptides, whereby the cargo peptides are isolated from the sample.

23. A method for isolating a plurality of cargo peptides from a serum sample, comprising:
   contacting a serum sample comprising cargo peptide-carrier protein complexes with an anion exchange moiety selective for at least one carrier protein, under conditions wherein the at least one carrier protein binds non-covalently to the anion exchange moiety, and wherein the anion exchange moiety is attached to a support;
   contacting the cargo peptide-carrier protein complexes with an elution solution having a pH greater than that of the sample, whereby the cargo peptides are dissociated from the cargo peptide-carrier protein complexes and the carrier proteins remain bound to the anion exchange moiety; and
   collecting the cargo peptides, whereby the cargo peptides are isolated from the serum sample.

* * * * *